(12) United States Patent
Faughnan et al.

(10) Patent No.: US 8,645,299 B2
(45) Date of Patent: Feb. 4, 2014

(54) METHOD, APPARATUS AND COMPUTER PROGRAM PRODUCT FOR CONTEXT BASED TAGGING OF DATA

(75) Inventors: John Faughnan, Saint Paul, MN (US); Keith Willard, St. Paul, MN (US)

(73) Assignee: McKesson Financial Holdings

( * ) Notice: Subject to any disclaimer, the term of this patent is extended or adjusted under 35 U.S.C. 154(b) by 615 days.

(21) Appl. No.: 12/650,785

(22) Filed: Dec. 31, 2009

(65) Prior Publication Data
US 2011/0161269 A1    Jun. 30, 2011

(51) Int. Cl.
*G06F 17/00* (2006.01)
*G06N 5/02* (2006.01)

(52) U.S. Cl.
USPC .............. 706/46; 600/300; 600/544

(58) Field of Classification Search
None
See application file for complete search history.

(56) References Cited

U.S. PATENT DOCUMENTS

| | | | |
|---|---|---|---|
| 6,063,028 A * | 5/2000 | Luciano | 600/300 |
| 2008/0125669 A1 * | 5/2008 | Suffin et al. | 600/544 |

* cited by examiner

*Primary Examiner* — Kakali Chaki
*Assistant Examiner* — Luis Sitiriche
(74) *Attorney, Agent, or Firm* — Alston & Bird LLP

(57) ABSTRACT

A method for enabling data interpretation includes receiving a plurality of data entries that are indicative of corresponding health care related events, determining an interest level rating for at least some of the data entries based at least in part on context information associated with a respective entity to which each data entry corresponds, and providing for presentation of selected data entries based on interest level rating. A corresponding computer program product and apparatus are also provided.

15 Claims, 3 Drawing Sheets

METHOD, APPARATUS AND COMPUTER PROGRAM PRODUCT FOR CONTEXT BASED TAGGING OF DATA

TECHNOLOGICAL FIELD

Figure 1:
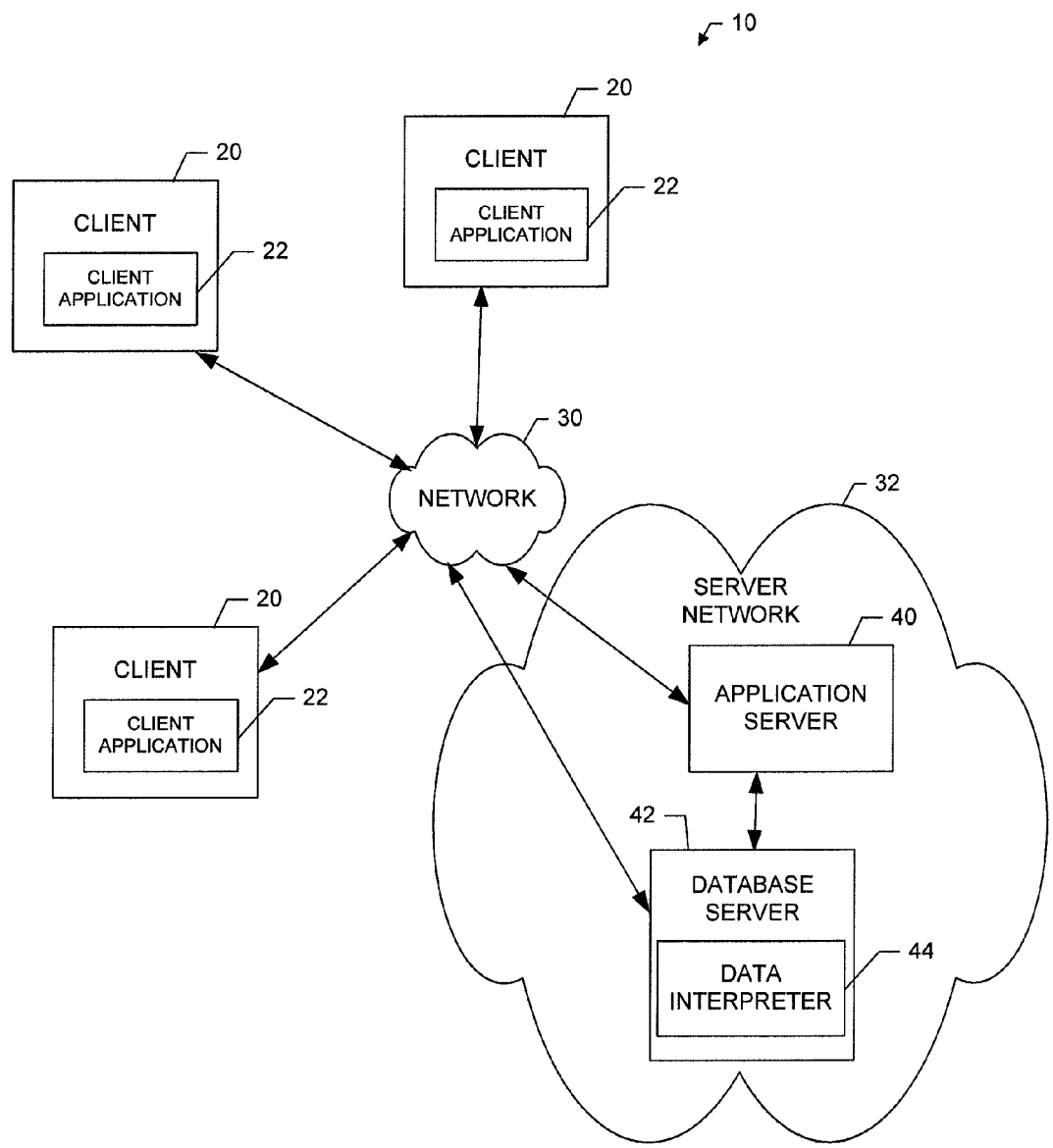

Embodiments of the present invention relate generally to health care management solutions and, more particularly, relate to a mechanism by which data may be tagged based on context in order to enable data that may be considered important in certain contexts (e.g., related to clinical medicine) to be identified and potentially presented to interested parties.

BACKGROUND

For many years, the mechanism for evaluating clinical processes related to a particular patient has been the medical chart or medical record. As such, for example, the medical record has been used to record patient identification, health history, medical examination and/or lab test results, medical prescriptions and other information such as, for example, orders related to the particular treatments or diagnoses associated with the patient. Accordingly, in order to assess whether a patient has received or is due to receive a particular treatment or care related event, the patient's chart would typically be reviewed. Additionally, in order to become aware of the results of various tests or treatments or to keep abreast of trends in certain indicators related to a particular condition or treatment, chart review would typically be required.

Recently, efforts have been made to move to electronic medical records (EMR). Although the EMR concept has encountered many issues in relation to, for example, cost, security, interoperability, etc., many hospitals are either employing, or planning to employ, some form of EMR. With clinical documentation systems moving to electronic media, clinical data may be available for incorporation into a number of different applications designed to assist in the management or use of such data. Computerized provider order entry (CPOE) is one example of a development that may improve the ability to electronically access information related to physician's orders. Many other applications are being developed to utilize electronic information on people and processes to manage the provision of various aspects of patient care including the provision of predictive care.

As the availability of electronic clinical data is increasing, the demand for applications that utilize such data to provide information, guidance and services is also increasing. Since many applications will require access to up to date or current care related information, the mechanism by which current and accurate information is provided to a variety of applications may become an important aspect in providing quality care management. However, even assuming a repository for current and accurate information can be provided, it may thereafter be difficult to digest all of the available data since some data is important in certain contexts, but relatively unimportant in other contexts.

Accordingly, it may be desirable to provide an improved mechanism by which clinical data that is important may be identified based on the context in which the data is provided.

BRIEF SUMMARY

A method, apparatus and computer program product are therefore provided to enable the provision of context-based tagging of information based on "universal concepts" comprising the basic structure (e.g., similar to "nouns" or "atoms") of predictive care protocols and rules used to enable subsequent distribution of some of the tagged information. In this regard, tagged information that is considered to be important based on the context in which such information is provided may be distributed as a subscribable event stream.

In one exemplary embodiment, a method for enabling data interpretation is provided. The method includes receiving a plurality of data entries that are indicative of corresponding health care related events, determining an interest level rating for at least some of the data entries based at least in part on context information associated with a respective entity to which each data entry corresponds, and providing for presentation of selected data entries based on interest level rating.

In another exemplary embodiment, a computer program product for enabling data interpretation is provided. The computer program product may include at least one computer-readable storage medium having computer-executable program code instructions stored therein. The computer-executable program code instructions may include program code instructions for receiving a plurality of data entries that are indicative of corresponding health care related events, determining an interest level rating for at least some of the data entries based at least in part on context information associated with a respective entity to which each data entry corresponds, and providing for presentation of selected data entries based on interest level rating.

In another exemplary embodiment, an apparatus for enabling data interpretation is provided. The apparatus may include processing circuitry. The processing circuitry may be configured for receiving a plurality of data entries that are indicative of corresponding health care related events, determining an interest level rating for at least some of the data entries based at least in part on context information associated with a respective entity to which each data entry corresponds, and providing for presentation of selected data entries based on interest level rating.

BRIEF DESCRIPTION OF THE SEVERAL VIEWS OF THE DRAWING(S)

Figure 2:
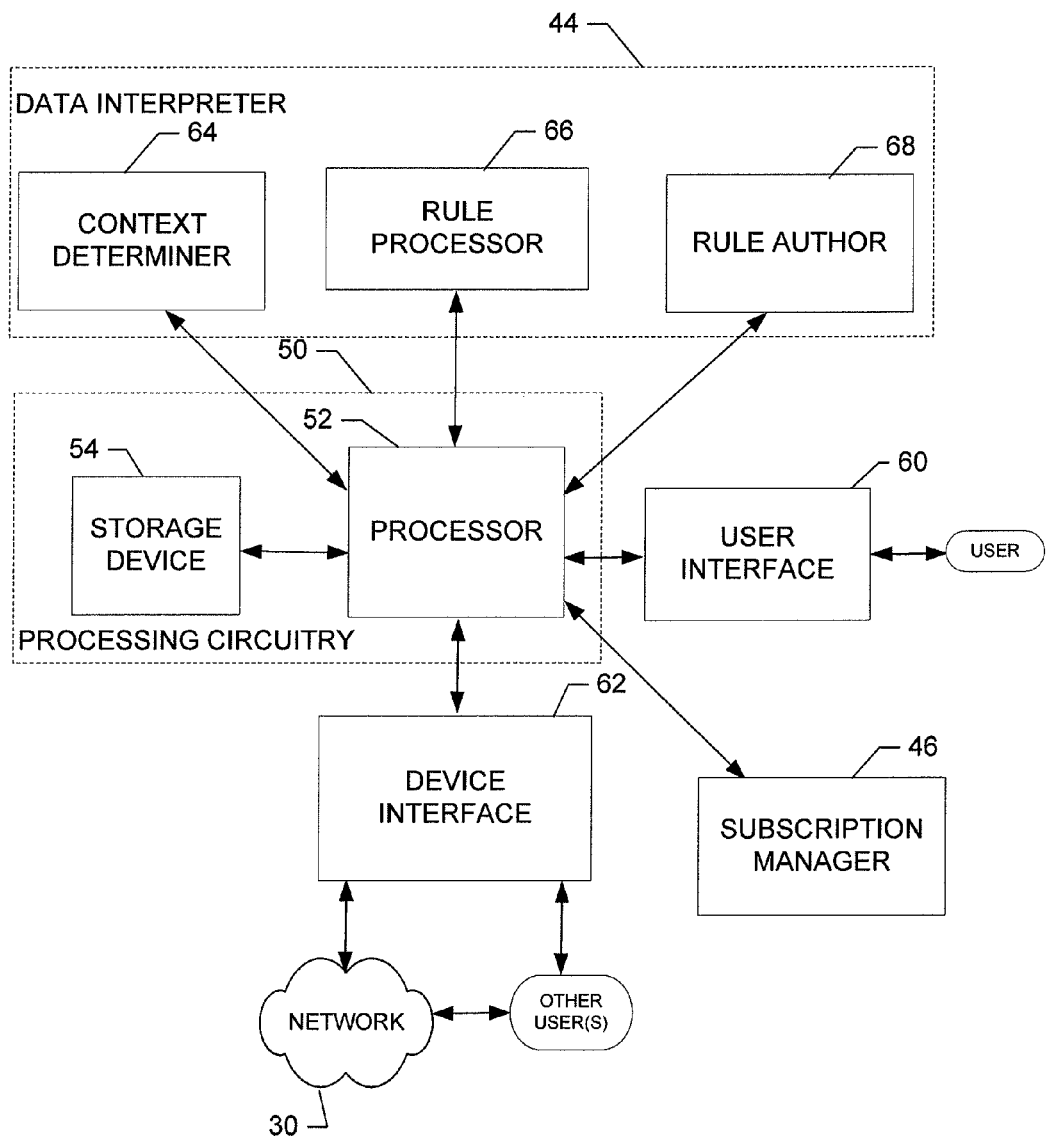
Figure 3:
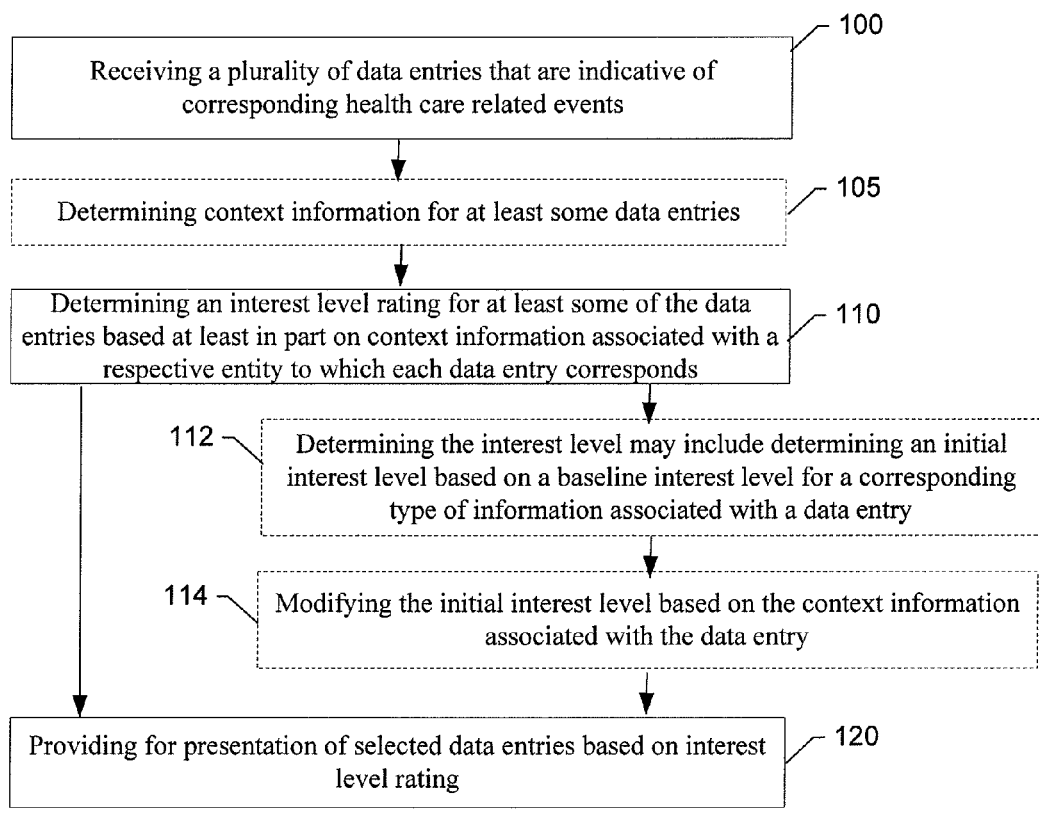

Having thus described embodiments of the invention in general terms, reference will now be made to the accompanying drawings, which are not necessarily drawn to scale, and wherein:

FIG. 1 is a block diagram illustrating a system for enabling data interpretation based at least in part on context according to an exemplary embodiment of the present invention;

FIG. 2 is a block diagram showing various components that may be included in an apparatus for enabling data interpretation based at least in part on context according to an exemplary embodiment of the present invention; and FIG. 3 is a block diagram according to an exemplary method for enabling data interpretation based at least in part on context according to an exemplary embodiment of the present invention.

DETAILED DESCRIPTION

Embodiments of the present invention will now be described more fully hereinafter with reference to the accompanying drawings, in which some, but not all embodiments of the invention are shown. Indeed, embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As indicated above, embodiments of the present invention are aimed at providing a mechanism by which the relative importance of information stored or otherwise provided in a fact repository may be determined. In order to provide such a determination, the information provided in the fact repository, which may be considered universal concepts or standardized statements about a patient, may be provided via subscribable data streams in which the data is tagged based on context. The universal concepts or facts may be linked to patients and computerized or rule based interpretation of actions, observations and/or other results may be provided.

Some universal concepts or statements of fact in the fact repository may be considered to be "interesting" or "important" in virtually all contexts. For example, a statement such as "fever present" or "blood culture negative" may usually or normally be considered interesting to a clinician or care provider. However, other universal concepts such as "blood pressure normal" may normally be of limited interest. Under normal circumstances, a human reviewing the statements above will make the determination as to whether information is interesting on a case by case basis. Thus, with the exception of certain facts that are almost always interesting, it may be difficult to provide a computerized or automated mechanism for assigning an interest level tag to selectively present information to a clinician without some human involvement to classify data.

Embodiments of the present invention may provide an automated mechanism by which interesting data may be determined based on context so that the data available via the fact repository is more likely to be useful information and can be provided in an appropriate form for consumption by users and other applications alike.

An exemplary embodiment of the invention will now be described in reference to FIG. 1, which illustrates an exemplary system in which an embodiment of the present invention may be employed. As shown in FIG. 1, a system according to an exemplary embodiment may include one or more clients 20 that may, in some cases, be associated with different corresponding units, wings or departments of a hospital or healthcare system. For example, one client 20 may be associated with a first hospital unit (e.g., an intensive care unit (ICU)) and a second client 20 may be associated with a second hospital unit (e.g., a respiratory therapy unit). However, information associated with multiple units may alternatively be accessible via a single client. Furthermore, in some cases, multiple clients may be associated with the same unit. In some examples, clients 20 could be located at nurse's stations, at various locations in hallways within a treatment unit, at a data entry location or even within patient rooms.

Each client 20 may be, for example, a computer (e.g., a personal computer, laptop computer, network access terminal, or the like) or may be another form of computing device (e.g., a personal digital assistant (PDA), cellular phone, or the like) capable of communication with a network 30. As such, for example, each client 20 may include (or otherwise have access to) memory for storing instructions or applications for the performance of various functions and a corresponding processor for executing stored instructions or applications. Each client 20 may also include software and/or corresponding hardware for enabling the performance of the respective functions of the clients as described below. In an exemplary embodiment, one or more of the clients 20 may include a client application 22 configured to enable one or more of various functions including, for example, data entry, information consumption, application execution, and/or the like. In this regard, for example, the client application 22 may include software for enabling a respective one of the clients 20 to communicate with the network 30 for the provision of and receipt of information associated with providing patient care. As such, for example, the client application 22 may include corresponding executable instructions for configuring the client 20 to provide corresponding functionalities for the provision of and receipt of information associated with receiving patient care data, processing patient care data and/or providing patient care data as described in greater detail below. Moreover, in an exemplary embodiment, the client application 22 may include functionality, either alone or in cooperation with other applications and/or processing devices, for providing context based tagging of data or consuming and/or presenting data based at least in part on context.

The network 30 may be a data network, such as a local area network (LAN), a metropolitan area network (MAN), a wide area network (WAN) (e.g., the Internet), and/or the like, which may couple the clients 20 to devices such as processing elements (e.g., personal computers, server computers or the like) or databases. Communication between the network 30, the clients 20 and the devices or databases (e.g., servers) to which the clients 20 are coupled may be accomplished by either wireline or wireless communication mechanisms and corresponding protocols. In an exemplary embodiment, the network 30 may include or otherwise be embodied as a communication bus, such as an enterprise service bus, to which various clients 20, computers, databases, servers or other like devices may be operably connected.

In an exemplary embodiment, one of the devices to which the clients 20 may be coupled via the network 30 may include one or more application servers (e.g., application server 40), and/or a database server 42, which together may form respective elements of a server network 32. Although the application server 40 and the database server 42 are each referred to as "servers", this does not necessarily imply that they are embodied on separate servers or devices. As such, for example, a single server or device may include both entities and the database server 42 could merely be represented by a database or group of databases physically located on the same server as the application server 40. The application server 40 and the database server 42 may each include hardware and/or software for configuring the application server 40 and the database server 42, respectively, to perform various functions. As such, for example, the application server 40 and the database server 42 may each include respective processing logic and memory enabling the application server 40 and the database server 42 to access and/or execute stored computer readable instructions for performing various functions. In an exemplary embodiment, one function that may be provided by the database server 42 may be the provision of a universal concept tagging on a context basis to enable certain interesting or important information to be provided to the clients 20. In this regard, for example, the database server 42 may include a data interpreter 44 comprising stored instructions for listening (e.g., via the enterprise service bus) for data being provided to the network (e.g., via clients 20) and determining whether the data is to be considered important or interesting based at least in part on the context associated with the data. Important or interesting data may be tagged as such and therefore be available for provision to interested parties that may subscribe to receive the data. As such, data provided to the database server 42 may essentially be filtered based on importance in a manner that considers the context of the data in determining the importance so that the information is available for use by other applications of the application server 40 or for access by the clients 20 as needed or otherwise desired.

Additionally or alternatively, the application server 40 may be configured to enable the clients 20 to provide information to the application server 40, for use by the application server 40 in producing, maintaining and/or supplying patient care information. In this regard, for example, the application server 40 (or servers) may include particular applications related to various different electronic medical record modules (e.g., CPOE or others). As such, some application servers may host data entry mechanisms that enable the entry of patient information, treatment information, test results, medical history, orders, medications, observations, and numerous other types of information for storage in the database server 42. The database server 42 may therefore form a fact repository to accept core clinical data updates of observations, medication administrations, intravenous (IV) administrations, orders and other similar data that may be provided in the context of an EMR or other hospital or healthcare system electronic data gathering and/or storage regimes. In some cases, the data to be stored in the fact repository may first be translated as appropriate by a translation layer that may include a mapping layer and a transform layer. The translation layer may provide a mechanism by which data entered into the system can be consistently translated prior to storage in the fact repository in order to provide a useful and accurate data repository.

In one embodiment, the fact repository may enhance patient data through associations with clinical concepts to form structured data. As a result of the associations with clinical concepts, the fact repository, which may in some cases include a processor and memory for enabling processing and storage, may process the patient data in various manners, such as by transforming the patient data to a standard representation. For example, in instances in which the data represents the patient's temperature, the fact repository may be configured to transform the temperature from a simple string representation, such as 101.9 F, to a strongly-typed internal, floating-point representation of the value. Through associations with clinical terms and rules related to the clinical terms, the fact repository may also determine one or more attributes associated with the transformed value. For example, the fact repository may, in the foregoing example, compare the transformed temperature value to a normal range of temperature values and determine if the patient's temperature is high, normal or low. These attributes may then be stored along with or otherwise in association with the patient data.

The fact repository may then process the structured data in accordance with rules associated with clinical concepts in order to further characterize and specify the nature of the patient data. For example, the fact repository may be configured to determine trends with respect to the patient data. The definition of a trend may be dependent upon the type of patient data. For example, with respect to body temperature, three consecutive body temperature recordings above the normal range within the preceding 12 hours may define a trend that creates an additional clinical fact that may be stored in addition to the underlying patient data. Similarly, temperatures above a certain level may, by correspondence with a rule defining temperatures associated with particular conditions, define a fever condition. Meanwhile, temperatures within a specific range may be defined to correspond to normal temperatures.

As indicated above, the fact repository may also include memory for storing the patient data, attributes related to the patient data and clinical facts that are created by analysis of the patient data. While the patient data may be stored within the memory of the fact repository while and at least shortly after the patient data is processed by the processor of the fact repository, other storage devices may also be provided, such as random access memory.

As indicated above, the database server 42 may act as a fact repository for electronically recorded clinical data regarding various activities performed with respect to a particular patient. In an exemplary embodiment, the clinical data that is written to the database server 42 may be mapped to a core-clinical ontology providing a framework for classifying the data. For example, a life-sciences ontology may be employed to provide a target representation of data for use in a patient quality monitor application. The core-clinical data may be transformed to a structured, strongly-typed form and represented as instances within the life-sciences model. Once transformed, the instances may be rationalized based on attributes such as normal, abnormal, outside normal range, within normal range, or other applicable attributes. Transformed and rationalized data may then be stored in the database server 42. In an exemplary embodiment, the database server 42 may comprise a long-term, persistent triple data store (TDS) that may be available for sending data to other applications as strongly-typed items.

Alternatively or additionally, the data stored in the database server 42 may be available for querying or searching and reporting or driving various applications. Once posted to the TDS, data can trigger or otherwise be used in connection with rule processing, including potentially complex rule processing, based on trigger mappings within the life-sciences model. As such, for example, a particular condition may be monitored by setting up rules that extract specific data from the database server 42 for use in various applications.

After data translation, which in some cases includes data classification, embodiments of the present invention may further provide for interpretation of some or all of the translated data. In an exemplary embodiment, the database server 42 may include the data interpreter 44 for performing such interpretation. After interpretation of the data, some embodiments of the present invention may further provide for selective display of some information based on the interpretation provided by the data interpreter 44. In an exemplary embodiment, the selective display may be provided in the form of one or more feeds to which a user may subscribe. Each subscribable feed may have a particular context or source associated therewith in order to enable users to have a robust control over the selection of information they would consider important or interesting so that data interpreted as being interesting to such users may be provide to them accordingly. In an exemplary embodiment, the selective display functionality may be provided by a subscription manager 46 described in greater detail below.

As indicated above, the data interpreter 44 may provide functionality for interpretation of data within the network 30 to ensure that the fact repository is not only populated with accurate and reliable information that is up to date, but also to enable interpretation of the data so that individual data consumers may be provided with corresponding data that each respective consumer considers important or interesting via the subscription manager 46. An exemplary embodiment of the invention will now be described with reference to FIG. 2. FIG. 2 shows certain elements of an apparatus for providing data interpretation based on context according to an exemplary embodiment. The apparatus of FIG. 2 may be employed, for example, on a variety of devices (such as, for example, a network device, server, proxy, or the like (e.g., the database server 42 of FIG. 1)). Alternatively, embodiments may be employed on a combination of devices. Accordingly, some embodiments of the present invention may be embodied wholly at a single device (e.g., the database server 42) or by devices in a client/server relationship (e.g., the database server 42 and one or more clients 20 or even the application server 40). Furthermore, it should be noted that the devices or elements described below may not be mandatory and thus some may be omitted in certain embodiments.

Referring now to FIG. 2, an apparatus for providing data interpretation based on context is illustrated by way of example. The apparatus may include or otherwise be in communication with processing circuitry 50 that is configured to perform data processing, application execution and other processing and management services according to an exemplary embodiment of the present invention. In one embodiment, the processing circuitry 50 may include a processor 52, a storage device 54 that may be in communication with or otherwise control a user interface 60 and a device interface 62. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, the user interface 60 may be disposed at another device (e.g., at a computer terminal or client device such as one of the clients 20) that may be in communication with the processing circuitry 50 via the device interface 62 and/or a network (e.g., network 30).

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, a cell phone, or other input/output mechanisms.

The device interface 62 may include one or more interface mechanisms for enabling communication with other devices and/or networks (e.g., via the bus). In some cases, the device interface 62 may be any means such as a device or circuitry embodied in either hardware, software, or a combination of hardware and software that is configured to receive and/or transmit data from/to a network and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an exemplary embodiment, the storage device 54 may include one or more memory devices such as, for example, volatile and/or non-volatile memory that may be either fixed or removable. The storage device 54 may be configured to store information, data, applications, instructions or the like for enabling the apparatus to carry out various functions in accordance with exemplary embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases (e.g., of the database server 42) that may store a variety of files, contents or data sets. Among the contents of the storage device 54, applications (e.g., the rational range transform manager 44) may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an exemplary embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an exemplary embodiment, the processor 52 (or the processing circuitry 50) may be embodied as, include or otherwise control the data interpreter 44, which may include, be in communication with, or in some cases control a context determiner 64, a rule processor 66 and, in some cases, a rule author 68. The example of FIG. 2 shows the context determiner 64, the rule processor 66 and the rule author 68 each being a portion of the data interpreter 44. However, in some cases, one or more of the context determiner 64, the rule processor 66 and the rule author 68 may be separate devices from the data interpreter 44.

The context determiner 64, the rule processor 66 and the rule author 68 may each be any means such as a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the context determiner 64, the rule processor 66 and the rule author 68, respectively, as described below.

The context determiner 64 may be configured to determine contextual information with respect to data provided to the network 30. In an exemplary embodiment, the context determiner 64 may be configured to listen to the bus (e.g., via the device interface 62) for data on the bus and determine indications of context associated with the data. In response to determining context information associated with clinical data on the bus (e.g., based on the enrollment of the patient in certain treatment protocols), the context determiner 64 may provide information indicative of the context associated with the data to the rule processor 66 to enable the rule processor 66 to handle the data based on the context information provided. As such, for example, the context information may be determined based on where the corresponding patient (e.g., the patient for which the data on the bus applies) is within the treatment protocol in which the patient is enrolled.

Context is generally defined as any information that can be used to characterize the situation of an entity. An entity may be a person, place or object (including data or information about a person, place or object) that is considered relevant to an interaction between a user and an application. Accordingly, a system may be considered context aware if the system uses context information to provide relevant information and/or services to the user such as where relevancy depends on the user's task. In a healthcare related environment, one example of a context aware system may be a system that is able to characterize the situation of a particular patient, the situation of a plurality of patients in a particular unit, or the situation of particular test results or other data.

In some embodiments, the context determiner 64 may be a context aware device or element configured to request context information or provide interface elements aimed at acquiring context information associated with data on the bus. In some cases, as indicated above, context information may be determined based on the enrollment of a patient within a particular treatment protocol, based on the orders provided for treatment or monitoring of a particular patient, based on factors such as time and/or frequency of acquisition of certain types of data, based on classifications associated with certain data and/or other factors. As such, the various treatment protocols may each be associated with a particular context by system designers in advance. In this regard, for example, during authoring, contexts may be assigned to various coded protocols that may be applied to patients. In some examples, the context determiner 64 may be configured to analyze various domains, fields, user interface elements and/or the like designed to enable a clinician entering data to characterize the data in some manner. The domains, fields, user interface elements and/or the like may be text entry based, predetermined selectable options, or customizable options that may change dependent upon user criteria (e.g., subscription level to a service, location, settings or preferences, etc.).

As an example, the context determiner 64 may have a mechanism by which the specific patient, unit, consultation, observation, clinician, order, or other characteristic to which a certain data entry pertains may be determined. As another example, various selectable common classifications for certain types of data may be provided. In some embodiments, the context determiner 64 may be configured to extract information from communications on the bus and, based on a predefined association for a particular patient based on the treatment protocol to which the patient is enrolled, determine a context for the particular object or data entry. As such, the situation of the patient relative to the protocol may be used to determine the context of data on the bus. Any other mechanism for discovering the context information may also be utilized. For example, the context determiner 64 may apply some natural language understanding technology to determine context information. The context information determined may then be provided to the rule processor 66. In some cases, the data to which context information applies may be tagged (e.g., by the context determiner 64) to provide an indication of the context associated with the corresponding data.

The rule processor 66 may be configured to correlate data entries with a corresponding interest level rating based on predefined rules. As such, for example, the rule processor 66 may receive a particular entry such as a temperature reading for a particular patient accompanied by context information determined by the context determiner 64. Notably, in some cases, the context information may actually include the identity of the particular patient among other things. One or more rules may be applied by the rule processor 66 in order to determine an interest level rating for the particular entry. The rules may define that certain entries are always of interest (with potential for exceptions), that certain entries are never of interest (with potential for exceptions), or that certain entries are of interest only in certain contexts. As such, the rule processor 66 may include a plurality of rules and a corresponding plurality of guidelines defining when such rules are applicable. In one embodiment, a mapping system may be utilized to map certain types of data to a corresponding rule or rule set. The rules or rule sets may include conditional or universal rules to particular types of data (e.g., rules based on processing particular lab results, physiological parameters, conditions, etc.). The conditional rules may apply, for example, Boolean expressions or other logical operators in order to determine whether the conditions for application of a corresponding rule apply. For example, a rule for body temperature may define that fever conditions are always of interest and that normal body temperature readings are only of interest under certain circumstances (e.g., as a recovery indicator from certain conditions for which the patient may have been treated). As such, for example, the rules may enable the assignment of an interest level attribute based on a clinical process data language code. Thus, when a fact flows through the system, the fact may be flagged as interesting by virtue of flowing through a protocol or by rule.

In some embodiments, the universal rules may include mapping certain types of data to an inherent interest level rating. In other words, some types of information may be structured to have an initial interest level rating associated therewith by virtue of the fact that such types of information are always (or nearly always) important and/or interesting events. The conditional rules may then work to modify the initial interest level rating in some cases. Thus, for example, a normally uninteresting event (e.g., an event with a relatively low initial interest level) may be modified based on context to have a higher interest level rating. Notably, the context information that forms the basis for adjusting, modifying or otherwise providing an indication of the interest level rating associated with a particular event is associated with the entity to which the event pertains. Thus, unlike most context related information provision services, which tend to be concerned with the context of the user receiving the information, embodiments of the present invention are concerned with the context of the entity to which the event pertains (e.g., the patient).

In some embodiments, the interest level rating may be a numerical value and a higher (or lower) numerical value may indicate a degree of interest associated with the corresponding data entry. As such, when determining which data to filter out for presentation later on, embodiments of the present invention may compare the numerical value to a threshold and designate for display (for a particular feed or notification service) only those data entries that exceed (or are below) a certain threshold. Alternatively, embodiments of the present invention may simply include a text ranking (e.g., important, not important or some similar go/no go rating system) for inclusion of data entries in corresponding feeds or notification services. Furthermore, since each feed or notification service may be topic specific and have different filtration or sorting algorithms associated therewith, it may be possible for the same data to be included in one feed (thereby indicating importance in one notification paradigm) and not included in another feed (thereby indicating unimportance in another notification paradigm).

Data processed by the rule processor 66 may receive a tag indicating an interest level rating for the corresponding data. As such, in some cases, all data may receive a tag and some tags may indicate a high level of interest, while others indicate varying other levels of interest. However, in some examples, data may only receive a tag at all if the data has been determined by the rule processor 66 to be data having a qualifying level of interest associated therewith based on application of the rules. As such, in some cases the tags may indicate a degree of interest, while in others the presence of a tag may be a go/no go indicator of interest level.

In some cases, the universal concept definition of a particular fact or data item on the bus may by itself be indicative of the interest level of the corresponding data item. As such, by default, certain types of data may be treated as being interesting. Such types of data, i.e., those types of data that are interesting under all circumstances by definition, may automatically be tagged accordingly by the rule processor 66. However, in some embodiments, it may not be necessary for the rule processor 66 to process data that is interesting by default. Other data for which a conditional rule is triggered based on context information associated with the data may have a tag applied only after the rule processor 66 determines that the context situation for which the data is considered interesting is currently in effect. Based on the interest level rating (e.g., as indicated by the tag associated with each data item or certain data items), data may be selected for publication or presentation to one or more users or user devices by the subscription manager 46 as described in greater detail below.

The predefined rules that are applied by the rule processor 66 may be provided via the rule author 68. In some embodiments, the rule author 68 may only be active or useable prior to deployment of the data interpreter 44. In other words, the predefined rules may be entirely predefined and unalterable when the data interpreter 44 is deployed. However, in other implementations, the rule author 68 may be an active module in a deployed data interpreter 44 to enable the user (e.g., a healthcare system administrator or even a clinician) to define some or all of the rules to be applied by the rule processor 66 in the field. Moreover, in some embodiments, specific doctors, nurses, or other care providers or managers may define specific rules for themselves and/or for their respective units or organizations. As such, rules employed by the rule processor 66 may, in some cases, be freely modified by users (or perhaps by users granted authoring authority) in order to enable great flexibility in terms of letting organizations or individuals tailor rule application to their unique respective situations and/or desires.

The rule author 68 may include a user interface template or rule definition wizard for enabling users to define rules and the results that are to ensue if a particular rule is triggered. As such, the rule author 68 may include popup windows, control consoles, text/data entry fields, hotspot selection options, menu options, Boolean expression generation interfaces, and/or other types of user interface mechanisms designed to enable users to flexibly define rules and consequences of rule application. Accordingly, the rule author 68 may be configured to enable the user to flexibly design a data filtering mechanism based at least in part on the context in which some data is received. After rules are defined, rules may be modified, activated and/or deactivated (e.g., in a rule activation/modification menu). Activated rules may be provided to the rule processor 66 for application of such rules to incoming data in conjunction with the corresponding context information associated with the incoming data. Based on the application of the rules by the rule processor 66 an interest level tag, or other indicator of level of interest associated with all or some of the data items. Data items may then be selectively presented to various users and/or devices based on the indicator or tag associated with respective items by the subscription manager 46.

The subscription manager 46 may be configured to sort data acted on by the rule processor 66 for selective presentation based on the interpretation of the results provided by the data interpreter 44. In this regard, for example, if the data interpreter 44 determines certain data to be important to one or more entities, such entities may be informed of the data by the subscription manager 46 in one of various different ways the subscription manager 46 may use to inform "subscribers". Subscribers may be entities (sometimes individual people and other times organizations, units or groups) that have provided the subscription manager 46 with an indication of their desire to be notified of certain types of information or at least of interesting information in certain circumstances.

In an exemplary embodiment, the subscription manager 46 may be configured to generate a plurality of feeds (e.g., RSS feeds) provided to subscribers to each respective feed. As such, for example, individual users or groups may subscribe to receive corresponding feeds of interest. Feeds may be organized based on many different criteria and a separate feed may be provided for one or more topics. As an example, feeds may be organized based on context, topic or source. Common sources may include a particular patient, a particular unit or organization, a particular consult, a particular clinician, and/or the like. Thus, for example, data corresponding to all patients in a wing, all patients associated with a particular doctor, all patients having a particular condition, or various combinations of context related characteristics may be organized into a feed and provided to subscribers of the corresponding feed. As such, the subscription manager 46 essentially filters data based on attributes associated with the data and provides the sorted data to parties indicating an interest in receiving such data. The filtered data may be filtered based on indications (e.g., associated with the attributes) that such data would be likely to be of interest to subscribers of the corresponding feed.

Alternatives to the feed subscriptions above may also be provided. For example, in some embodiments, the subscription manager 46 may take subscriptions to a broadcast service that sends broadcast emails or other broadcast messages to subscribers. SMS or text messages and other communication mechanisms may alternatively be employed as well in some cases. In an exemplary embodiment, an application (e.g., a web application) may be provided with corresponding links to different topics. In response to selection of a link, a window may be opened to display real time or historical data that is applicable to the topic selected. As yet another alternative, a timeline application may be provided to show information for a particular patient or associated with a particular topic in a timeline fashion. In one or more of the examples above, icons may be provided in place of data or to augment data that is presented. In such examples, the icons may provide an indication of the type of data presented (e.g., each type of data may have a corresponding icon associated therewith) or the particular event with which the icon is associated. The icons may alternatively or additionally indicate whether the data is indicative of a normal or abnormal reading or situation. In cases where the icons are shown instead of the actual data, selecting an icon may trigger the presentation of the corresponding data. In other situations, icons may link users to related data such as more detailed information about the corresponding patient, condition, event or treatment protocol with which the icon is associated. As such, numerous options may be provided for the manner in which information is provided to subscribers by the subscription manager 46.

Some embodiments of the present invention may therefore enable organizations to provide a consistent and up to date data repository with comprehensive data stored therein and further provide notifications of selected data entries to interested parties in an automated fashion. The mechanism for providing the notifications may be constructed to determine an interest level rating associated with various date entries and present selected ones of the data entries based on the interest level ratings. The presentation may be accomplished based on subscriptions that various individuals may submit to corresponding feeds or notification services.

Embodiments of the present invention may therefore be practiced using an apparatus such as the one depicted in FIG. 2. However, other embodiments may be practiced in connection with a computer program product for performing embodiments of the present invention. FIG. 3 is a flowchart of a method and program product according to exemplary embodiments of the invention. Each block or step of the flowchart of FIG. 3, and combinations of blocks in the flowchart, may be implemented by various means, such as hardware, firmware, processor, circuitry and/or another device associated with execution of software including one or more computer program instructions. Thus, for example, one or more of the procedures described above may be embodied by computer program instructions, which may embody the procedures described above and may be stored by a storage device (e.g., storage device 54) and executed by processing circuitry (e.g., processor 52).

As will be appreciated, any such stored computer program instructions may be loaded onto a computer or other programmable apparatus (i.e., hardware) to produce a machine, such that the instructions which execute on the computer or other programmable apparatus implement the functions specified in the flowchart block(s) or step(s). These computer program instructions may also be stored in a computer-readable medium comprising memory that may direct a computer or other programmable apparatus to function in a particular manner, such that the instructions stored in the computer-readable memory produce an article of manufacture including instructions to implement the function specified in the flowchart block(s) or step(s). The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

In this regard, a method according to one embodiment of the invention, as shown in FIG. 3, may include receiving a plurality of data entries that are indicative of corresponding health care related events at operation 100 and determining an interest level rating for at least some of the data entries based at least in part on context information associated with a respective entity to which each data entry corresponds at operation 110. The method may further include providing for presentation of selected data entries based on interest level rating at operation 120.

In some cases, the method may include additional optional operations, examples of which are shown in dashed lines in FIG. 3. In this regard, in an exemplary embodiment, the method may further include determining context information for at least some data entries prior to determining the interest level at operation 105. In some embodiments, determining the interest level may include several sub-operations. As an example, in some cases, determining the interest level may include determining an initial interest level based on a baseline interest level for a corresponding type of information associated with a data entry at operation 112, and modifying the initial interest level based on the context information associated with the data entry at operation 114.

In some embodiments, various ones of the operations described above may be modified. The modifications may generally occur in any combination and in any order. In this regard, for example, determining the context information may include, for each entity, determining the context information based on a treatment protocol into which the entity is enrolled. In some embodiments, providing for presentation may include providing selected data entries having an interest level rating that triggers presentation for the selected data entries. Alternatively or additionally, providing for presentation may include sorting the data entries into a plurality of feeds based on the interest level rating of each data entry and presenting each feed to a respective group of subscribers to a corresponding feed. As yet another alternative or additional option, providing for presentation may include providing a timeline view of events with icons associated with at least some of the events.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for enabling data interpretation comprising:

receiving, via one or more processors, a plurality of data entries that are indicative of corresponding health care related events;

determining, via the one or more processors, context information for at least some of the plurality of data entries;

determining, via the one or more processors, an interest level rating for the at least some of the data entries based at least in part on the context information associated with a respective entity to which each data entry corresponds; and providing, via the one or more processors, for presentation of selected data entries to a user based on the respective interest level ratings, wherein providing for presentation comprises providing for presentation of only the selected data entries of the at least some of the data entries having an interest level rating that triggers presentation of the selected data entries to the user.

2. The method of claim 1, wherein determining an interest level comprises:

determining an initial interest level based on a baseline interest level for a corresponding type of information associated with a data entry; and modifying the initial interest level based on the context information associated with the data entry.

3. The method of claim 1, wherein determining the context information comprises, for each entity, determining the context information based on a treatment protocol into which the entity is enrolled.

4. The method of claim 1, wherein providing for presentation comprises sorting the data entries into a plurality of feeds based on the interest level rating of each data entry and presenting each feed to a respective group of subscribers to a corresponding feed.

5. The method of claim 1, wherein providing for presentation comprises providing a timeline view of events with icons associated with at least some of the events.

6. A computer program product for enabling data interpretation, the computer program product comprising at least one non-transitory computer-readable storage medium having computer-executable program code instructions stored therein, the computer-executable program code instructions comprising:

program code instructions for receiving a plurality of data entries that are indicative of corresponding health care related events;

program code instructions for determining context information for at least some of the plurality of data entries;

program code instructions for determining an interest level rating for the at least some of the data entries based at least in part on the context information associated with a respective entity to which each data entry corresponds; and program code instructions for providing for presentation of selected data entries to a user based on the respective interest level ratings, wherein providing for presentation comprises providing for presentation of only the selected data entries of the at least some of the data entries having an interest level rating that triggers presentation of the selected data entries to the user.

7. The computer program product of claim 6, wherein program code instructions for determining an interest level comprises program code instructions for:

determining an initial interest level based on a baseline interest level for a corresponding type of information associated with a data entry; and modifying the initial interest level based on the context information associated with the data entry.

8. The computer program product of claim 6, wherein determining the context information comprises, for each entity, determining the context information based on a treatment protocol into which the entity is enrolled.

9. The computer program product of claim 6, wherein program code instructions for providing for presentation include instructions for sorting the data entries into a plurality of feeds based on the interest level rating of each data entry and presenting each feed to a respective group of subscribers to a corresponding feed.

10. The computer program product of claim 6, wherein program code instructions for providing for presentation include instructions for providing a timeline view of events with icons associated with at least some of the events.

11. An apparatus for enabling data interpretation comprising processing circuitry configured to:

receive a plurality of data entries that are indicative of corresponding health care related events;

determine context information for at least some of the plurality of data entries;

determine an interest level rating for the at least some of the data entries based at least in part on the context information associated with a respective entity to which each data entry corresponds; and provide for presentation of selected data entries to a user based on the respective interest level ratings, wherein providing for presentation comprises providing for presentation of only the selected data entries of the at least some of the data entries having an interest level rating that triggers presentation of the selected data entries to the user.

12. The apparatus of claim 11, wherein the processing circuitry is configured to determine an interest level by:

determining an initial interest level based on a baseline interest level for a corresponding type of information associated with a data entry; and modifying the initial interest level based on the context information associated with the data entry.

13. The apparatus of claim 11, wherein the processing circuitry is configured to determine the context information by, for each entity, determining the context information based on a treatment protocol into which the entity is enrolled.

14. The apparatus of claim 11, wherein the processing circuitry is configured to provide for presentation by sorting the data entries into a plurality of feeds based on the interest level rating of each data entry and presenting each feed to a respective group of subscribers to a corresponding feed.

15. The apparatus of claim 11, wherein the processing circuitry is configured to provide for presentation by providing a timeline view of events with icons associated with at least some of the events.

* * * * *